US012751680B2

(12) United States Patent
Moriyasu

(10) Patent No.: US 12,751,680 B2
(45) Date of Patent: Oct. 6, 2026

(54) NUCLEAR MEDICINE DIAGNOSTIC APPARATUS, NUCLEAR MEDICINE IMAGING METHOD AND COMPUTER READABLE NON-VOLATILE STORAGE MEDIUM STORING NUCLEAR MEDICINE IMAGING PROGRAM

(71) Applicant: CANON MEDICAL SYSTEMS CORPORATION, Otawara (JP)

(72) Inventor: Kenta Moriyasu, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 428 days.

(21) Appl. No.: 18/349,210

(22) Filed: Jul. 10, 2023

(65) Prior Publication Data

US 2024/0041414 A1 Feb. 8, 2024

(30) Foreign Application Priority Data

Aug. 2, 2022 (JP) ................................ 2022-123052

(51) Int. Cl.
*A61B 6/00* (2024.01)
*A61B 6/04* (2006.01)
*A61B 6/42* (2024.01)

(52) U.S. Cl.
CPC .......... *A61B 6/4452* (2013.01); *A61B 6/0407* (2013.01); *A61B 6/0487* (2020.08); *A61B 6/4258* (2013.01)

(58) Field of Classification Search
CPC ............................ A61B 6/4258; A61B 6/4452
See application file for complete search history.

(56) References Cited

U.S. PATENT DOCUMENTS

2015/0094571 A1* 4/2015 Bouhnik .............. A61B 6/4258 600/425
2019/0076110 A1 3/2019 Moriyasu

FOREIGN PATENT DOCUMENTS

JP S61-181385 U 11/1986
JP 7005240 B2 1/2022

OTHER PUBLICATIONS

Office Action issued May 12, 2026, in corresponding Japanese Patent Application No. 2022-123052 with English translation, citing documents 1 and 3 therein, 5 pages.
Li et al. "Image Reconstructions from Super-Sampled Data Sets in PET Imaging", 2013 IEEE Nuclear Sciences Symposium and Medical Imaging Conference (2013 NSS/MIC), 2013.

* cited by examiner

*Primary Examiner* — Dani Fox
(74) *Attorney, Agent, or Firm* — Oblon, McClelland, Maier & Neustadt, L.L.P.

(57) ABSTRACT

A nuclear medicine diagnostic apparatus according to an embodiment includes a nuclear medicine detector and processing circuitry. The nuclear medicine detector includes a plurality of detection devices that detect gamma rays. The processing circuitry controls a change from a first relative position of the nuclear medicine detector and a subject to a second relative position that is separate from the first relative position by a distance smaller than a device size of the detection device, collects first data in the first relative position, collects second data in the second relative position, and reconstructs a nuclear medicine image based on the first data and the second data.

6 Claims, 7 Drawing Sheets

NUCLEAR MEDICINE DIAGNOSTIC APPARATUS, NUCLEAR MEDICINE IMAGING METHOD AND COMPUTER READABLE NON-VOLATILE STORAGE MEDIUM STORING NUCLEAR MEDICINE IMAGING PROGRAM

CROSS-REFERENCE TO RELATED APPLICATIONS

This application is based upon and claims the benefit of priority from Japanese Patent Application No. 2022-123052, filed on Aug. 2, 2022, the entire contents of which are incorporated herein by reference.

FIELD

Embodiments described herein relate generally to a nuclear medicine imaging apparatus, a nuclear medicine imaging method, and a computer readable non-volatile storage medium storing a nuclear medicine imaging program.

BACKGROUND

As for recent nuclear medicine diagnostic apparatuses, there is a trend that more segmented scintillators are used and upsampling is performed by computation by artificial intelligence (AI) and thus the pixel size of nuclear medicine images is reduced.

Manufacturing a segmented scintillator however is difficult and a low yield of segmented scintillators in manufacturing sometimes increases the manufacturing cost. When upsampling of the pixel size is executed by computation, segmented pixel information is predicted values and therefore accuracy of an image associated with upsampling sometimes lowers.

DETAILED DESCRIPTION

A nuclear medicine diagnostic apparatus includes a nuclear medicine detector and processing circuitry. The nuclear medicine detector includes a plurality of detection devices that detect gamma rays. The processing circuitry controls a change from a first relative position between the nuclear medicine detector and a subject to a second relative position that is separate from the first relative position by a distance smaller than a device size of the detection device, collects first data in the first relative position, collects second data in the second relative position, and reconstructs a nuclear medicine image based on the first data and the second data.

With reference to the accompanying drawings, the nuclear medicine diagnostic apparatus, a nuclear medicine imaging method, and a nuclear medicine imaging program will be described in detail below. In the following embodiment, constituents denoted with the same reference numbers are supposed to perform the same operations and redundant description is omitted properly. The nuclear medicine diagnostic apparatus, the nuclear medicine imaging method, and the nuclear medicine imaging program are not limited to the following embodiment.

The nuclear medicine diagnostic apparatus according to the embodiment includes an imaging system that performs position emission tomography (PET) imaging. For example, a PET apparatus that has only a PET imaging function, a PET-CT apparatus having the PET imaging system and an X-ray computed tomography (CT) imaging system, and a PET-MR apparatus including the PET imaging system and a magnetic resonance (MR) imaging system are taken as such nuclear medicine diagnostic apparatuses. The nuclear medicine diagnostic apparatus according to the embodiment may include an imaging system that performs single photon emission CT (SPECT) imaging. For example, a SPECT apparatus including only a SPECT imaging system, a SPECT-CT apparatus including the SPECT imaging system, and a SPECT-MR apparatus including the SPECT imaging system and an MR imaging system are taken as such nuclear medicine diagnostic apparatuses.

The nuclear medicine diagnostic apparatus according to the embodiment is applicable to an apparatus of any of the aforementioned types; however, in order to provide specific description below, the nuclear medicine diagnostic apparatus is supposed to be a PET-CT apparatus.

Embodiment

Figure 1:
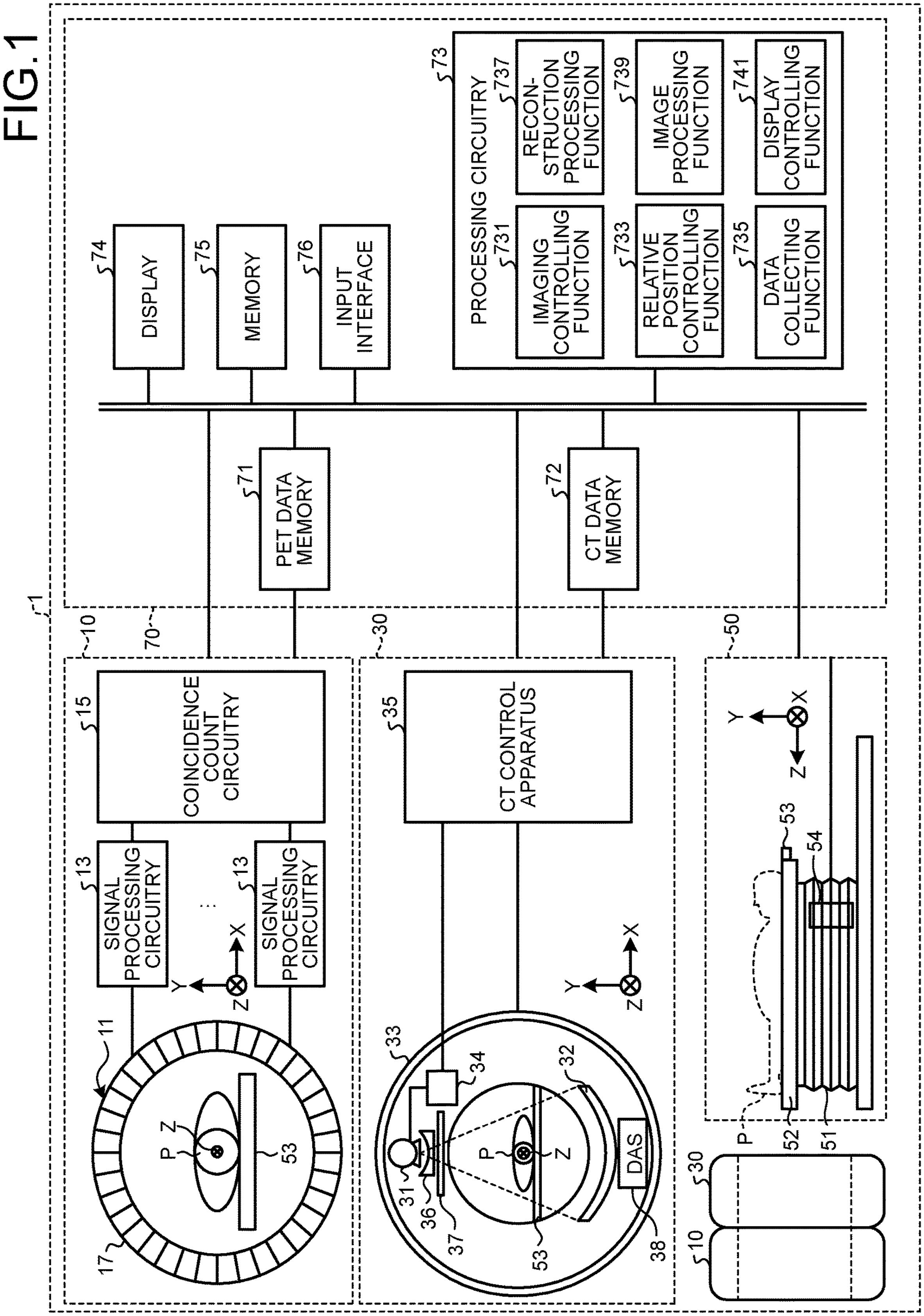
FIG. 1 is a diagram illustrating an example of a PET-CT apparatus 1 according to an embodiment.

FIG. 1 is a diagram illustrating an example of a configuration of a PET-CT apparatus 1 according to an embodiment. As illustrated in FIG. 1, the PET-CT apparatus 1 includes a PET gantry 10, a CT gantry 30, a table 50, and a console 70. Typically, the PET gantry 10, the CT gantry 30, and the table 50 are set in a common examination room. The console 70 is set in a control room adjacent to the examination room. The PET gantry 10 is an imaging apparatus for performing PET imaging (PET scan) on a subject P. The CT gantry 30 is an imaging apparatus for performing X-ray CT imaging (CT scan) on the subject P. The table 50 movably supports a tabletop 53 on which the subject P on which imaging is to be performed is laid. The console 70 is a computer that controls the PET gantry 10, the CT gantry 30, and the table 50.

As illustrated in FIG. 1, the PET gantry 10 includes, for example, a detector ring 11, signal processing circuitry 13, and coincidence count circuitry 15. The PET gantry 10 and the CT gantry 30 may be housed in the same casing.

The detector ring 11 includes a plurality of gamma ray detectors 17 that are arrayed on a circumference on a center axis Z. A plurality of the detector rings 11 may be arrayed along a longitudinal axial direction (a Z-direction) of the tabletop 53. For convenience of description below, the detector rings 11 are supposed to be arrayed in the Z-direction below. The gamma ray detector 17 corresponds to a nuclear medicine detector.

A field of view (FOV) is set in an opening of the detector ring 11. The subject P is positioned such that a portion of the subject P to be imaged is contained in the FOV. An agent that is labelled with positron-emitting radionuclides is applied to the subject P. A positron that is emitted from the positron-emitting radionuclide annihilates with a surrounding electron. Annihilation causes annihilation gamma rays in a pair. The gamma ray detectors 17 detects the annihilation gamma rays that are emitted from the inside of the subject P. The gamma ray detector 17 generates an electric signal corresponding to the optical amount of the detected annihilation gamma ray. For example, the gamma ray detector 17 includes a plurality of scintillators and a plurality of photomultiplier tubes. On receiving an annihilation gamma ray that derives from a radioisotope in the subject P, the scintillator generates scintillation light. The scintillators correspond to a plurality of detection devices that detect gamma rays. The gamma ray detector 17 includes the detection devices. The photomultiplier tube generates an electric signal corresponding to the optical amount of the scintillation light. The generated electric signal is supplied to the signal processing circuitry 13. The gamma ray detector 17 may be realized by a DOI detector capable of discriminating a depth of interaction (referred to as "DOI" below).

The signal processing circuitry 13 generates single event data based on the electric signal that is output from the gamma ray detector 17. Specifically, the signal processing circuitry 13 performs detection time measurement processing, position calculation processing, and energy calculation processing on the electric signal. The signal processing circuitry 13 is realized by an application specific integrated circuit (ASIC), a field programmable gate array (FPGA), another complex programmable logic device (CPLD), and a simple programmable logic device (SPLD) that are configured to be able to execute the detection time measurement processing, position calculation processing, and energy calculation processing.

In the detection time measurement processing, the signal processing circuitry 13 measures a time of detection of the gamma ray by the gamma ray detector 17. Specifically, the signal processing circuitry 13 monitors a crest value of the electric signal from the gamma ray detector 17 and measures, as the time of detection, a time at which the crest value exceeds a threshold that is set previously. In other words, the signal processing circuitry 13 senses that the crest value exceeds the threshold, thereby electrically detecting the annihilation gamma ray. In the position calculation processing, the signal processing circuitry 13 calculates a position of incidence of the annihilation gamma ray based on the electric signal from the gamma ray detector 17. The position of incidence of the annihilation gamma ray corresponds to the coordinates of the position of the scintillator on which the annihilation gamma ray is incident. In the energy calculation processing, the signal processing circuitry 13 calculates an energy value of the detected annihilation gamma ray based on the electric signal from the gamma ray detector 17.

Data of the time of detection, data of the coordinates of the position, and data of the energy value on the single event are associated with one another. The combination of the data of the energy value, the data of the coordinates of the position, and the data of the time of detection on the single event is referred to as single event data. Single event data is generated every time an annihilation gamma ray is detected. The generated single event data is supplied to the coincidence count circuitry 15.

The coincidence count circuitry 15 performs coincidence count processing on the single event data from the signal processing circuitry 13. As for hardware resources, the coincidence count circuitry 15 is realized by an ASIC, a FPGA, a CPLD, or a SPLD that is configured to be able to execute the coincidence count processing. In the coincidence count processing, the coincidence count circuitry 15 repeatedly specifies single event data on two single events that are within a predetermined time frame among sets of single event data that are repeatedly supplied. It is estimated that the single events in a pair derive from annihilation gamma rays that are generated from the same annihilation point. The single events in a pair are collectively referred to as a coincidence count event. A line connecting the gamma ray detectors 17 (more specifically, scintillators) that detect the annihilation gamma rays is referred to as a line of response (LOR). The event data on the events in a pair forming the LOR is referred to as coincidence count event data. The coincidence count event data and the single event data are transmitted to the console 70. The coincidence count event data and the single event data are collectively referred to as PET event data when not particularly distinguished from each other.

Note that, in the above-described configuration, the signal processing circuitry 13 and the coincidence count circuitry 15 are included in the PET gantry 10 and the present embodiment is not limited to this. For example, the coincidence count circuitry 15 or both the signal processing circuitry 13 and the coincidence count circuitry 15 may be included in an apparatus independent of the PET gantry 10. The single coincidence count circuitry 15 may be provided for a plurality of sets of the signal processing circuitry 13 that is mounted on the PET gantry 10 or the sets of the signal processing circuitry 13 mounted on the PET gantry 10 are divided into multiple groups and the coincidence count circuitry 15 may be provided for each of the groups.

As illustrated in FIG. 1, the CT gantry 30 includes an X-ray tube 31, an X-ray detector 32, a rotation frame 33, an X-ray high-voltage apparatus 34, a CT control apparatus 35, a wedge 36, a collimator 37, and a DAS 38.

The X-ray tube 31 generates an X-ray. Specifically, the X-ray tube 31 includes a vacuum tube that has a cathode that generates a thermal electron and an anode that generates an X-ray on receiving the thermal electron flying from the cathode. The X-ray tube 31 is connected to the X-ray high-voltage apparatus 34 via a high-voltage cable. The X-ray high-voltage apparatus 34 applies the tube voltage between the cathode and the anode. Application of the tube voltage causes the thermal electron to fly from the cathode to the anode. The thermal electron flies from the cathode to the anode and accordingly a tube current flows. Application of the high-voltage and application of a filament current from the X-ray high-voltage apparatus 34 causes a thermal electron to fly from the cathode to the anode and the thermal electron crushes against the anode. Accordingly, an X-ray is generated.

The X-ray detector 32 detects the X-rays that are generated from the X-ray tube 31 and that have passed through the subject P. The X-ray detector 32 outputs an electric signal corresponding to the dose the detected X-rays to the DAS 38. The X-ray detector 32 has a configuration in which a plurality of X-ray detection device arrays in which a plurality of X-ray detection devices are arrayed in a channel direction are arrayed in a slice direction (a column direction or a row direction). The X-ray detector 32 is, for example, an indirect conversion detector including a grid, a scintillator array, and an optical sensor array. The scintillator array includes a plurality of scintillators. The scintillator outputs light of a photon quantity corresponding to a dose of an incident X-ray. The grid is arranged on a surface of the scintillator array on the side of incidence of the X-ray. The grid includes an X-ray shield that absorbs scattering X-rays. An optical sensor array converts light that is output from the scintillator into an electric signal corresponding to the amount of the light. For example, a photodiode or a photomultiplier tube is used as the optical sensor. The X-ray detector 32 may be realized by a direct conversion detector (semiconductor detector) including a semiconductor device that converts an incident X-ray into an electric signal.

The rotation frame 33 is an annular frame that supports the X-ray tube 31 and the X-ray detector 32 rotatably on a rotation axis Z. Specifically, the rotation frame 33 supports the X-ray tube 31 and the X-ray detector 32 such that the X-ray tube 31 and the X-ray detector 32 are opposed to each other. The rotation frame 33 is supported by a fixed frame (not illustrated in the drawings) rotatably on the rotation axis Z. Under the control of the CT control apparatus 35, the rotation frame 33 rotates on the rotation axis Z. Accordingly, the X-ray tube 31 and the X-ray detector 32 rotate on the rotation axis Z. On receiving a power from a drive mechanism of the CT control apparatus 35, the rotation frame 33 rotates on the rotation axis Z at a given angular speed. An FOV is set in an opening of the rotation frame 33.

In the embodiment, a rotation axis of the rotation frame 33 in a non-tilt state or a longitudinal direction of the tabletop 53 of the table 50 is a Z-axis direction (the Z-direction), an axial direction orthogonal to the Z-axis direction and that is parallel to a floor surface is an X-axis direction (an X-direction), and an axial direction that is orthogonal to the Z-axis direction and that is perpendicular to the floor surface is a Y-axis direction (a Y-direction).

The X-ray high-voltage apparatus 34 includes electric circuits, such as a transformer and a rectifier. The X-ray high-voltage apparatus 34 includes a high-voltage generation device that generates a high voltage to be applied to the X-ray tube 31 and an X-ray control device that performs control on an output voltage corresponding to the X-ray that is applied by the X-ray tube 31. The high-voltage generation device may employ a transformer method or an inverter method. The X-ray high-voltage apparatus 34 may be provided in the rotation frame 33 in the CT gantry 30 or may be provided in a fixed frame (not illustrated in the drawing) in the CT gantry 30.

The wedge 36 adjusts the dose of X-rays to be applied to the subject P. Specifically, the wedge 36 attenuates the X-rays to be applied from the X-ray tube 31 to the subject P such that the X-rays have a predetermined distribution. For example, a metal board of aluminum, or the like, such as a wedge filter or a bow-tie filter, is used as the wedge 36.

The collimator 37 limits an area to which the X-rays having transmitted through the wedge 36 are applied. The collimator 37 supports a plurality of lead plates that block X-rays slidably and adjusts a form of a slit that is formed by the lead plates.

The data acquisition system (DAS) 38 reads, from the X-ray detector 32, the electric signal corresponding to the dose of the X-rays that are detected by the X-ray detector 32. The DAS 38 amplifies the read electric signal at an amplifying rate. The DAS 38 then integrates amplified electric signals over a view period, thereby collecting CT raw data having a digital value corresponding to the dose of X-rays over the view period. The DAS 38 is realized by, for example, an ASIC on which a circuit device capable of generating CT raw data is mounted. The CT raw data is transmitted to the console 70 via a non-contact data transmission apparatus, or the like.

The CT control apparatus 35 controls the X-ray high-voltage apparatus 34 and the DAS 38 in order to execute X-ray CT imaging using an imaging controlling function 731 of processing circuitry 73 of the console 70. The CT control apparatus 35 includes a processing circuit including a central processing unit (CPU) and a drive system, such as a motor and an actuator. The processing circuit includes, as hardware resources, a processor, such as a CPU or a micro-processing unit (MPU), and a memory, such as a read only memory (ROM) or a random access memory (RAN). The CT control apparatus 35 may be realized by an ASIC, a FPGA, a CPLD, a SPLD, or the like.

As for the CT gantry 30, there are various types like a Rotate/Rotate-type (a third-generation CT) in which an X-ray generator and an X-ray detector uniformly rotate around the subject P and a Stationary/Rotate-type (a fourth-generation CT) in which only an X-ray generator rotates around the subject P, and any of the types is applicable to an embodiment.

As illustrated in FIG. 1, the subject P to be scanned is laid on the table 50 and the laid subject P is caused to move on the table 50. The table 50 is shared by the PET gantry 10 and the CT gantry 30.

The table 50 includes a base 51, a support frame 52, the tabletop 53 and a table drive apparatus 54. The base 51 is set on the floor surface. The base 51 is a chassis that supports the support frame 52 movably in a direction (the Y-axis direction) orthogonal to the floor surface. The support frame 52 is a frame that is provided on the top of the base 51. The support frame 52 supports the tabletop 53 slidably along the center axis Z. The tabletop 53 is a board that is flexible and on which the subject P is laid.

The table drive apparatus 54 is housed in the chassis of the table 50. The table drive apparatus 54 is a motor or an actuator that generates a power for causing the support frame 52 and the tabletop 53 on which the subject P is laid to move. The table drive apparatus 54 operates according to the control of the console 70, etc.

The PET gantry 10 and the CT gantry 30 are arranged such that the center axis Z of the opening of the PET gantry 10 and the center axis Z of the opening of the CT gantry 30 approximately coincide. The table 50 is arranged such that the longitudinal axis of the tabletop 53 is parallel with the center axis Z of the openings of the PET gantry 10 and the CT gantry 30. The CT gantry 30 and the PET gantry 10 are set, for example, from the side close to the table 50 in the following order: the CT gantry 30 and the PET gantry 10.

As illustrated in FIG. 1, the console 70 includes a PET data memory 71, a CT data memory 72, the processing circuitry 73, a display 74, a memory 75, and an input interface 76. For example, data communication between the PET data memory 71, the CT data memory 72, the processing circuitry 73, the display 74, the memory 75, and the input interface 76 is performed via a bus.

The PET data memory 71 is a storage apparatus that stores the single event data and the coincidence count event data that are transmitted from the PET gantry 10. The PET data memory 71 is a storage device, such as a hard disk drive (HDD), a solid state drive (SSD), or an integrated circuit storage apparatus.

The CT data memory 72 is a storage apparatus that stores the CT raw data that is transmitted from the CT gantry 30.

The CT data memory 72 is a storage apparatus, such as a HDD, SDD, or an integrated circuit storage apparatus.

The processing circuitry 73 includes, as hardware resources, a processor, such as a CPU, a MPU, or a graphics processing unit (GPU), and a memory, such as a ROM or a RAM. The processing circuitry 73 executes various types of programs that are read from the memory, thereby implementing the imaging controlling function 731, a relative position controlling function 733, a data collecting function 735, a reconstruction process function 737, an image processing function 739, and a display controlling function 741. In other words, the processing circuitry 73 corresponds to a processor that implements the functions corresponding to the respective programs by reading the programs from the memory and executing the programs. In other words, the processing circuitry 73 having read each program has the function corresponding to the read program. Note that the imaging controlling function 731, the relative position controlling function 733, the data collecting function 735, and the reconstruction process function 737, the image processing function 739, and the display controlling function 741 may be implemented dispersedly by the processing circuitry 73 of a single board or may be implemented by the processing circuitry 73 of a plurality of boards. The processing circuitry 73 that implements the imaging controlling function 731, the relative position controlling function 733, the data collecting function 735, and the reconstruction process function 737, the image processing function 739, and the display controlling function 741 corresponds to each of an imaging controller, a relative position controller, a data collector, a reconstruction processor, and an image processor, and a display controller.

In the imaging controlling function 731, the processing circuitry 73 synchronously controls the PET gantry 10 and the table 50 in order to perform PET imaging. The PET imaging according to the embodiment is intermittent move scans (step and shoot method) of collecting PET event data per collecting area while intermittently moving the tabletop 53. The processing circuitry 73 controls the CT gantry 30 and the table 50 synchronously to perform CT imaging. To perform PET imaging and CT imaging sequentially, the imaging controlling function 731 controls the PET gantry 10, the CT gantry 30, and the table 50 synchronously. The processing circuitry 73 is capable of executing the positioning scan (referred to as a PET positioning scan below) by the PET gantry 10 or a positioning scan by the CT gantry 30 (referred to as a CT positioning scan below). For a PET positioning scan, the processing circuitry 73 controls the PET gantry 10 and the table 50 synchronously. For a CT positioning scan, the processing circuitry 73 controls the CT gantry 30 and the table 50 synchronously.

In the relative position controlling function 733, the processing circuitry 73 controls a change from a first relative position between the gamma ray detector 17 (the nuclear medicine detector) and the subject P to a second relative position distant from the first relative position by a distance smaller than the device size of the scintillator (the detection device). The first relative position, for example, corresponds to a relative positional relationship (a first relative positional relationship) of the subject P (or the tabletop 53) to the position of the gamma ray detector 17. The second relative position, for example, corresponds a relative positional relationship (second relative positional relationship) of the position of the subject P (or the tabletop 53) to the position of the gamma ray detector 17 distant from the first relative position by a distance smaller than the device size of the scintillator (detection device). Control by the relative position controlling function 733, for example, is executed in a single shoot (a scan execution position) in intermittent move scans. In other words, when a plurality of shoots are executed in intermittent move scans, the relative position controlling function 733 controls a change in the relative position from the first relative position to the second relative position in each shoot in the intermittent move scans. In other words, when a shoot is made only once, the relative position controlling function 733 controls the change from the first relative position to the second relative position in the single shoot.

Specifically, in changing the relative position from the first relative position to the second relative position (in other words, changing the relative positional relationship), the relative position controlling function 733 controls move of at least one of the gamma ray detector 17 and the tabletop 53 on which the subject P is laid. For example, the relative position controlling function 733 controls move of at least one of the gamma ray detector 17 and the tabletop 53 along a direction (referred to as a move direction below) including at least one of a vertical direction (the Y-direction), the longitudinal direction of the tabletop 53 (the Z-direction), and a transverse direction of the tabletop 53 (the X-direction). For example, the relative position controlling function 733 controls the table drive apparatus 54, thereby moving the tabletop 53 from the first relative position to the second relative position along a direction that is set by the user via the input interface 76. Accordingly, the relative positional relationship of the subject P (or the tabletop 53) to the gamma ray detector 17 is changed from the first relative positional relationship to the second relative positional relationship.

The relative position controlling function 733, for example, controls a ring move system that is provided in the PET gantry 10, thereby moving the gamma ray detector 17 from the first relative position to the second relative position along a direction that is set by the user. The ring move system is a system causes the detector ring 11 to move in the PET gantry 10 under the control of the relative position controlling function 733. The configuration of the ring move system can be realized by various types of motors, various types of guides, etc., and therefore description thereof will be omitted. The PET gantry 10 may include a PET gantry move system that causes the PET gantry 10 to move. In that case, the relative position controlling function 733 controls the PET gantry move system, thereby causing the PET gantry 10 to moving along a direction that is set by the user. Accordingly, the gamma ray detector 17 may be moved from the first relative position to the second relative position.

As described above, changing from the first relative position to the second relative position is realized by moving at least one of the tabletop 53 and the gamma ray detector 17.

Figure 2:
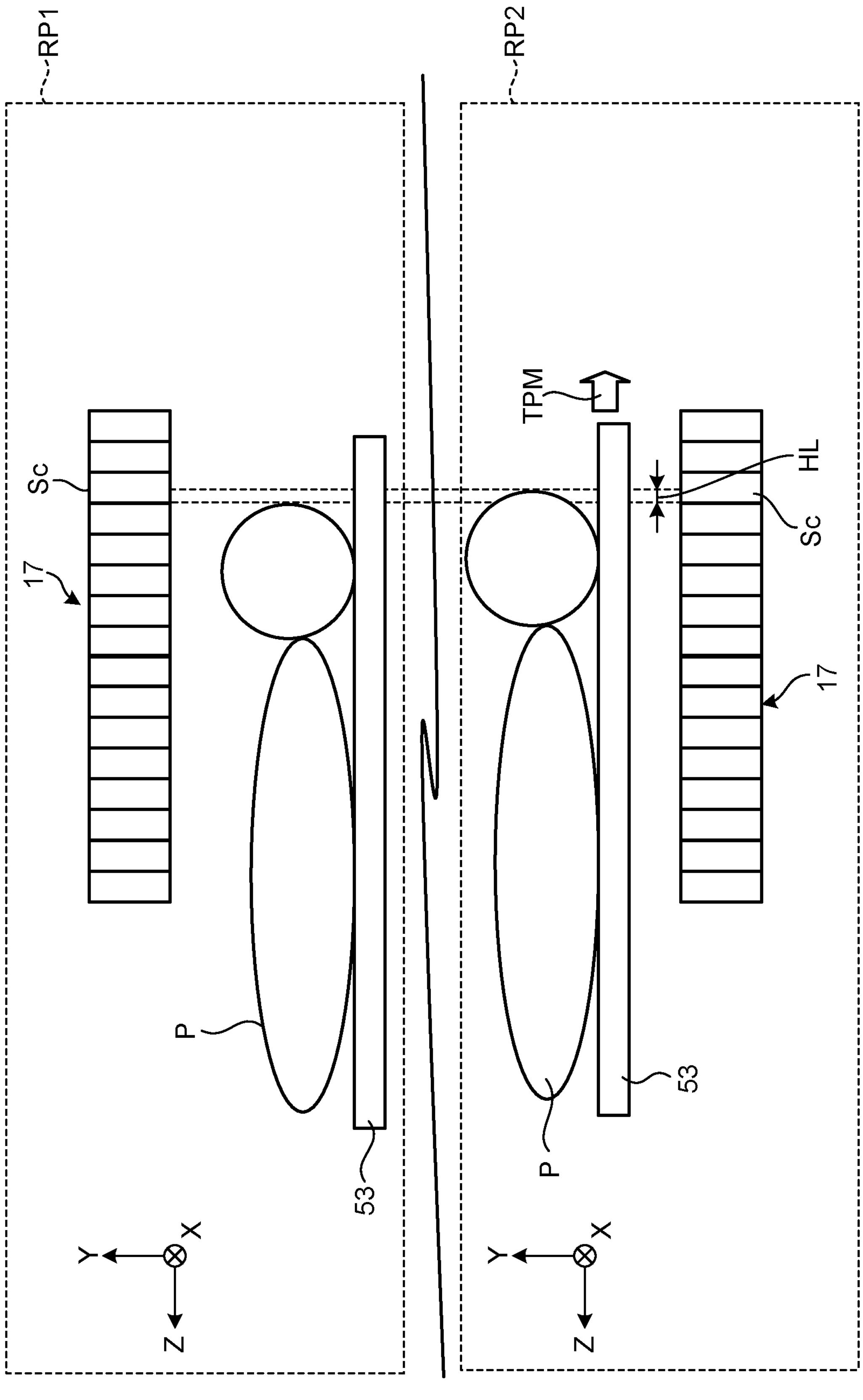
FIG. 2 is a diagram illustrating an example of a first relative position and a second relative position in a single shoot in intermittent move scans according to the embodiment.

FIG. 2 is a diagram illustrating an example of a first relative position RP1 and a second relative position RP2 in a single shoot in intermittent move scans. As illustrated in FIG. 2, in a single shoot in intermittent move scans, a move TPM of the tabletop 53 causes a change from the first relative position RP1 to the second relative position RP2. FIG. 2 presents that a distance of move of the tabletop 53 is a length HL that is a half of the width of a scintillator Sc (length of the surface of incidence of gamma rays) in the gamma ray detector 17; however, the distance of move is not limited to this, and the distance may be set freely as long as the distance is shorter than the width of the scintillator Sc.

In the data collecting function 735, the processing circuitry 73 collects first data in the first relative position and collects second data in the second relative position. The first data and the second data are, for example, coincidence count event data corresponding to each of the first relative position and the second relative position. The data collecting function 735 may collect second data while sequentially changing the relative position from the first relative position to the second relative position. The data collecting function 735 generates upsampling data whose data density is higher than those of the first data and the second data based on the first relative position and the second relative position and the first data and the second data and saves the upsampling data in the memory 75. The data collecting function 735 stores the upsampling data, for example, in the memory 75.

Figure 3:
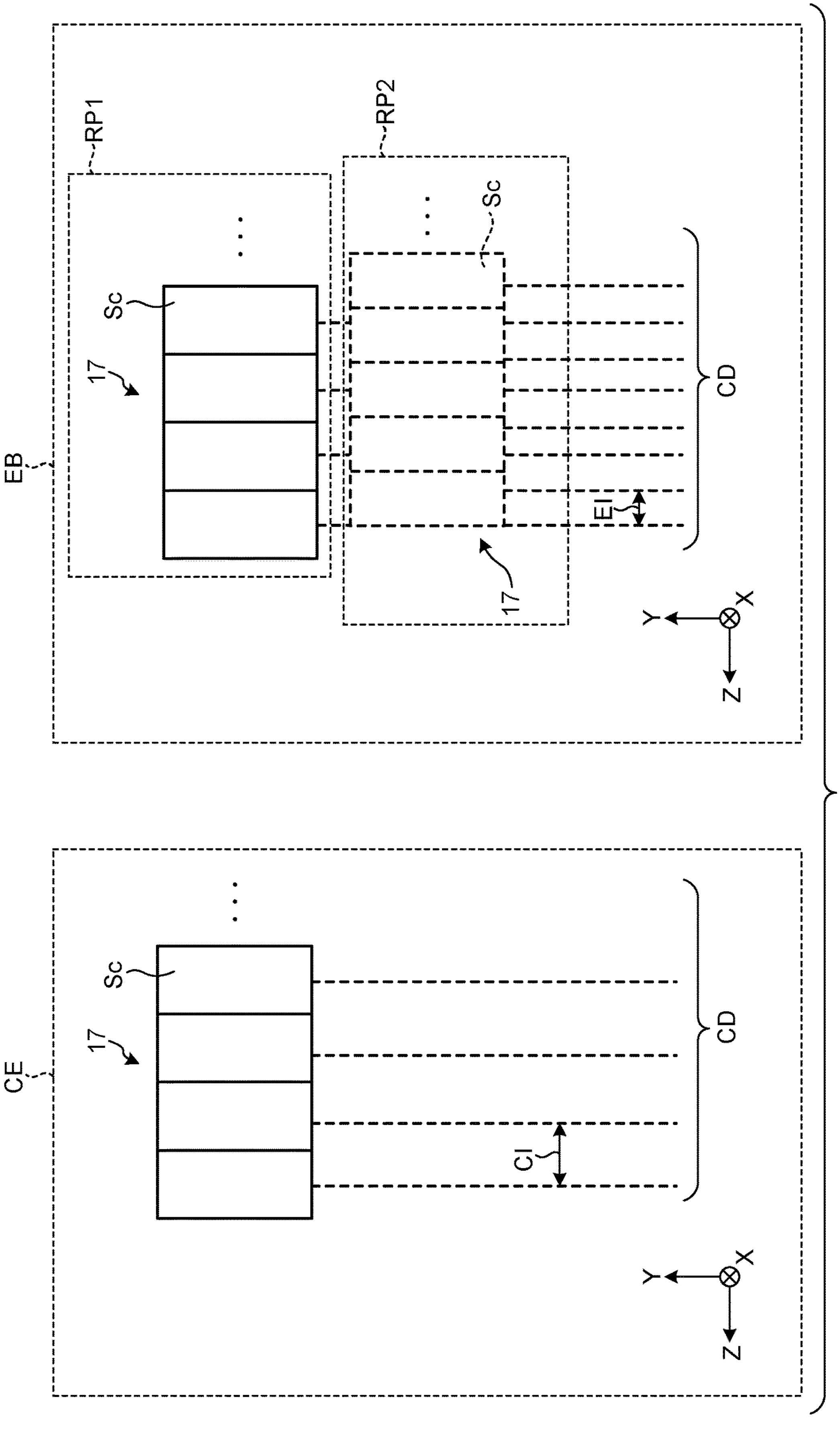
FIG. 3 is a diagram illustrating an example of sets of data collected with respect to a comparative example and the embodiment according to the embodiment in a single shoot in intermittent move scans according to the embodiment.

FIG. 3 is a diagram illustrating an example of sets of data collected with respect to a comparative example CE and the embodiment EB in a single shoot in intermittent move scans (referred to as an S&S collecting method below). In the S&S collecting method illustrated in FIG. 3, the gamma ray detector 17 in the second relative position RP2 is moved in the Z-direction with respect to the first relative position RP1 differently from that in FIG. 2 to simplify the description. As illustrated in FIG. 3, an interval EI between sets of collected data CD based on gamma rays incident on the scintillators in the embodiment EB is narrower than an interval CI in the comparative example CE and is half the interval CI in the comparative example. For this reason, in the embodiment, the density of the obtained data is doubled in one shoot. Thus, in the embodiment, it is possible to acquire data more densely than in the conventional comparative example.

For example, to collect data while moving the tabletop 53 in a smaller area than the size of the detection device (scintillator Sc) (referred to as a sequential collecting method below), the data collecting function 735 saves raw data larger in size and more densely than the raw data that is defined by the detection device (the first data and the second data), for example, in a given storage site in the memory 75. In other words, in the sequential collecting method, when storing raw data, the data collecting function 735 saves the raw data densely compared to the size that is defined by the scintillator Sc. In this case, the data collecting function 735 allocates the raw data (the first data and the second data) to storage sites in the memory 75 according to the positions of collection of gamma rays in the first relative position and the second relative position, that is, the positions of the scintillators Sc.

Specifically, based on the first relative position and the second relative position (or a distance of move from the first relative position to the second relative position) and the ID of the detection device (the scintillator Sc), the data collecting function 735 determines storage positions to which the first data and the second data are allocated. Note that the data collecting function 735 may allocate the first data and the second data to the determined positions of allocation. The data collecting function 735 may determine storage sites of allocation further using the first data and the second data. The data collecting function 735 executes allocation of data to storage sites using a nearest position, computation, and a trained model, such as a neural network. The computation is, for example, centroid computation. Inputs and outputs of the trained model correspond to inputs and outputs of the computation and a computation process is realized using the trained model.

Figure 4:
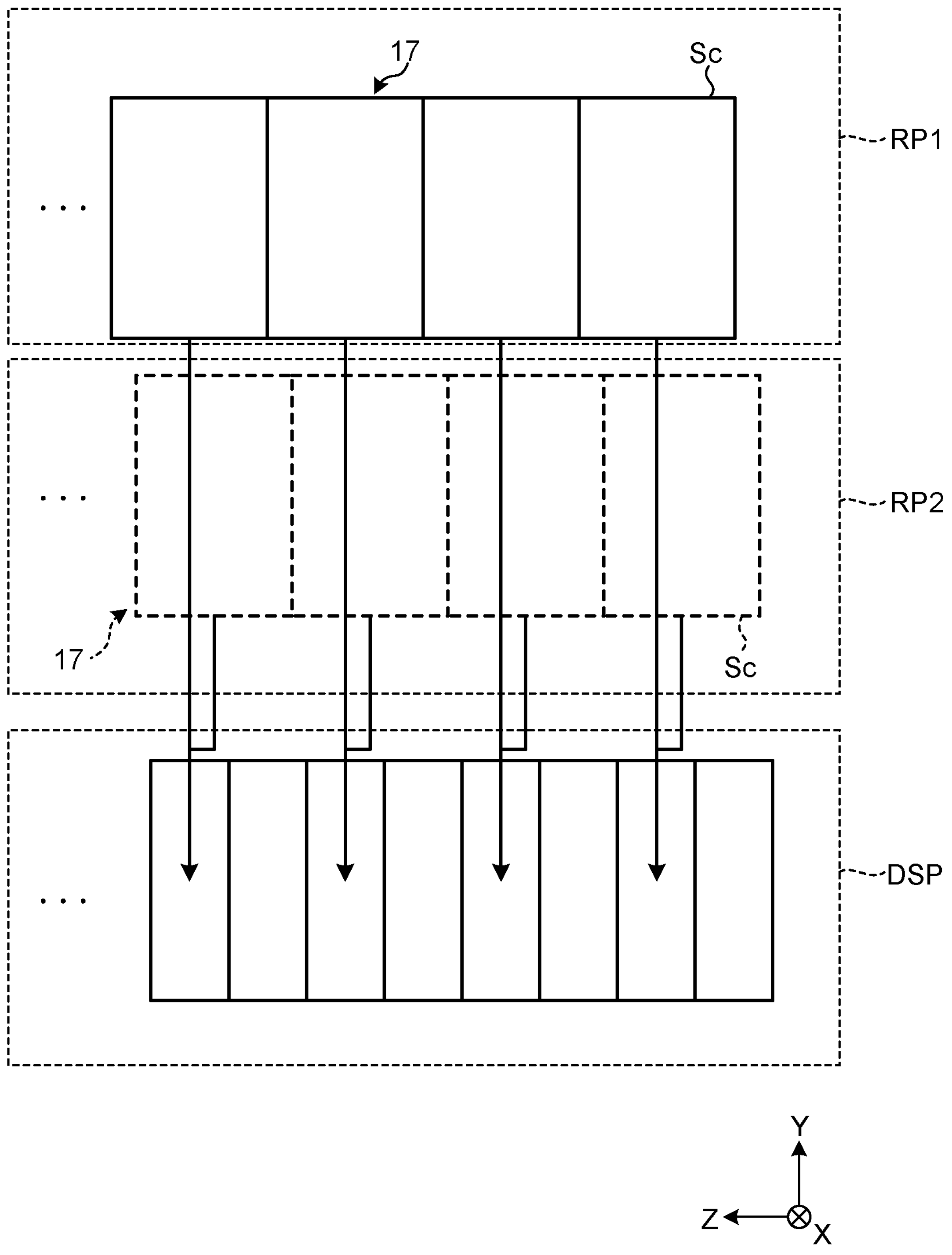
FIG. 4 is a diagram illustrating an example of a storage site according to allocation of data with respect to first data and second data on upsampling according to the embodiment.
Figure 5:
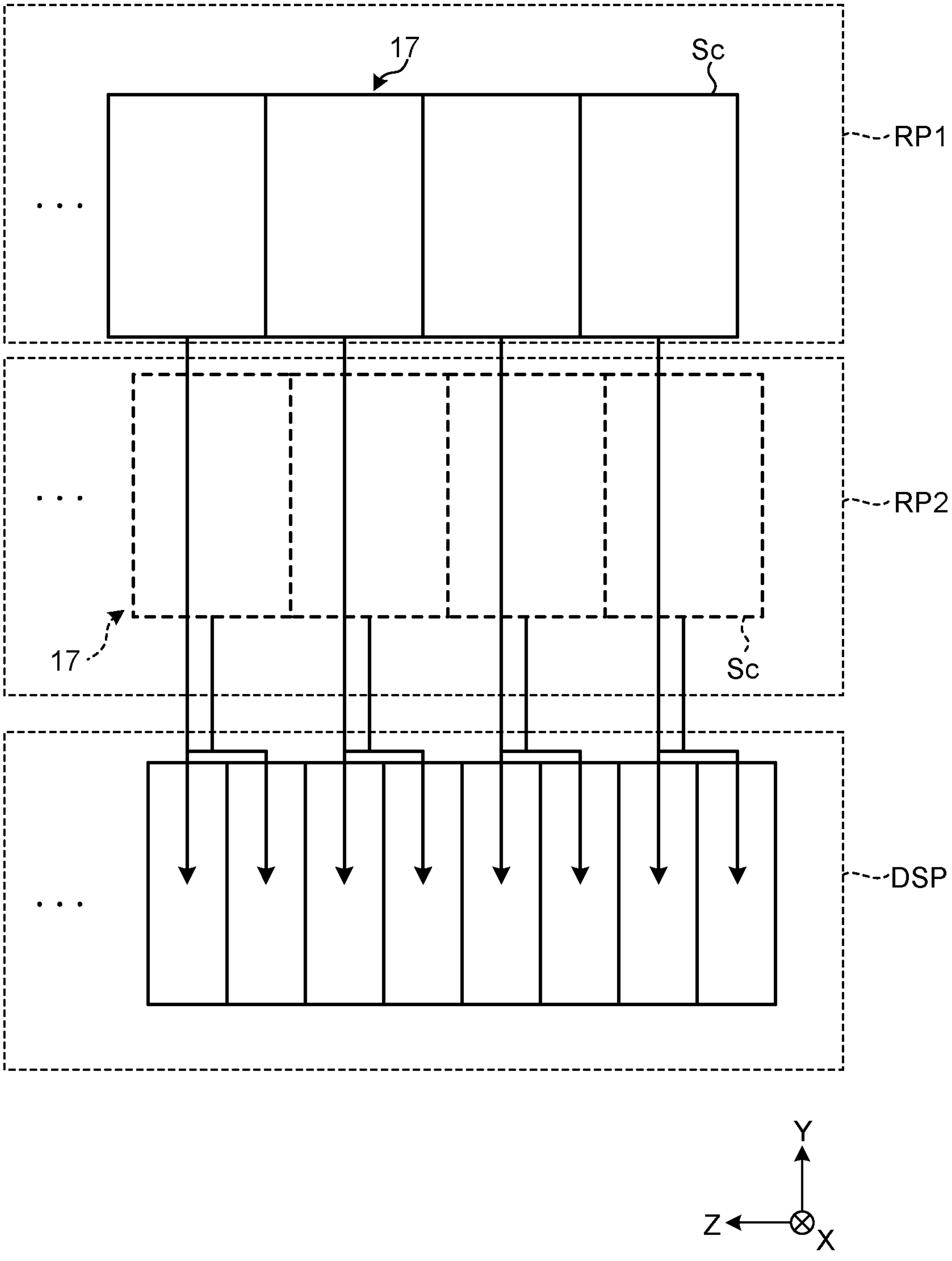
FIG. 5 is a diagram illustrating an example of a storage according to allocation of data with respect to first data and second data on upsampling according to a modification of the embodiment according to the embodiment.

FIG. 4 and FIG. 5 are diagrams illustrating an example of a storage site DSP according to allocation of the data with respect to the first data and the second data on upsampling by the data collecting function 735. FIG. 4 illustrates an example of allocation of the first data and the second data to storage sites corresponding to the nearest positions of the respective scintillators. A known method of nearest neighbor adjacency is usable as appropriate to determine storage sites corresponding to the nearest positions and thus description thereof is omitted.

FIG. 5 illustrates an example in which the first data and the second data with respect to each of the scintillators are allocated to the storage sites that are determined by computation or the trained model. The data collecting function 735 inputs, for example, the first relative position, the second relative position (or the distance of move from the first relative position to the second relative position) and the ID of the detection device (the scintillator Sc) to the computation or the trained model and a given calculation determines storage sites for the first data and the second data. The first data and the second data may be further input to the computation or the trained model.

In the reconstruction process function 737, based on the coincidence count event data, the processing circuitry 73 reconstructs a PET image presenting a distribution of positron-emitting radionuclides that are applied to the subject P. Based on the CT raw data, the processing circuitry 73 reconstructs a CT image that expresses a spatial distribution of CT values with respect to the subject P. An existing image reconstruction algorithm, such as a filtered back projection (FBP) method or a successive approximation reconstruction method, may be used as an image reconstruction algorithm. The processing circuitry 73 is able to generate a positioning image with respect to PET based on PET event data and generate a positioning image with respect to CT based on the CT raw data.

By the reconstruction process function 737, the processing circuitry 73 reconstructs a nuclear medicine image (for example, a PET image) based on the first data and the second data. Specifically, the reconstruction process function 737 reconstructs a nuclear medicine image using upsampling data based on the first data and the second data. As for the method of reconstructing a nuclear medicine image, because a known method, such as FBP or successive approximation reconstruction, is applicable as required, description thereof will be omitted.

In the image processing function 739, the processing circuitry 73 performs various sets of image processing on the PET image and the CT image that are reconstructed by the reconstruction process function 737. For example, the processing circuitry 73 performs three-dimensional image processing, such as volume rendering, surface volume rendering, pixel value projection processing, multi-planer reconstruction (MPR) processing, and CPR (curved MPR) processing, on the PET image and the CT image to generate a display image.

In the display controlling function 741, the processing circuitry 73 displays various sets of information on the display 74. For example, the processing circuitry 73 displays the PET image and the CT image that are reconstructed by the reconstruction process function 737. Prior to execution of PET imaging, the processing circuitry 73 displays a setting screen for selecting a collecting area, times of collecting in the first relative position and the second relative position, and a collecting method (the S&S or sequential method) in PET imaging.

The display 74 displays various sets of information under the control of the processing circuitry 73. For example, a cathode ray tube (CRT) display, a liquid crystal display (LCD), organic electro luminescence display (OELD), a light emitting diode (LED) display, a plasma display or another freely-selected display known in the art is usable as appropriate as the display 74. The display 74 may be a desktop display or may be configured using a tablet terminal device, or the like, capable of wirelessly communicating with the console 70.

The memory 75 is a storage apparatus, such as a HDD, a SSD, or an integrated circuit storage apparatus, that stores various sets of information. The memory 75 may be a drive device that reads and writes various sets of information from and in a portable storage medium, such as a compact disc (CD)-ROM drive, a digital versatile disc (DVD) drive, or a flash memory, or the like. The memory 75 stores various types of data on execution of an imaging controlling function 731, a relative position controlling function 733, the data collecting function 735, the reconstruction process function 737, the image processing function 739, and the display controlling function 741. The memory 75 stores upsampling data based on the first data and the second data that are collected by execution of PET scans on the subject P. The memory 75 stores various types of programs on execution of the imaging controlling function 731, the relative position controlling function 733, the data collecting function 735, the reconstruction process function 737, the image processing function 739, and the display controlling function 741. The memory 75 stores a computation process or a trained model that is used for high-definition image generation process to be described below.

The input interface 76 receives various types of input operations from the user, converts the received input operations into electric signals, and outputs the electric signals to the processing circuitry 73. For example, a mouse, a keyboard, a trackball, a switch, a button, a joystick, a touch pad and a touch panel display, or the like, is usable as appropriate as the input interface 76. In the embodiment, the input interface 76 is not limited to ones including physical operational parts, such as a mouse, a keyboard, a trackball, a switch, a button, a joystick, a touch pad and a touch panel display, or the like. For example, examples of the input interface 76 include an electric signal circuitry that receives an electric signal corresponding to an input operation from an external input device that is provided independently of the apparatus and outputs the electric signal to the processing circuitry 73. The input interface 76 may be configured of a tablet terminal device capable of wireless communication with the console 70, or the like.

An entire configuration of the PET-CT apparatus 1 has been described. A process of generating high-definition PET images (nuclear medicine images) by executing data collection in the first relative position and the second relative position (referred to as the high-definition image generation process below) will be described below.

Figure 6:
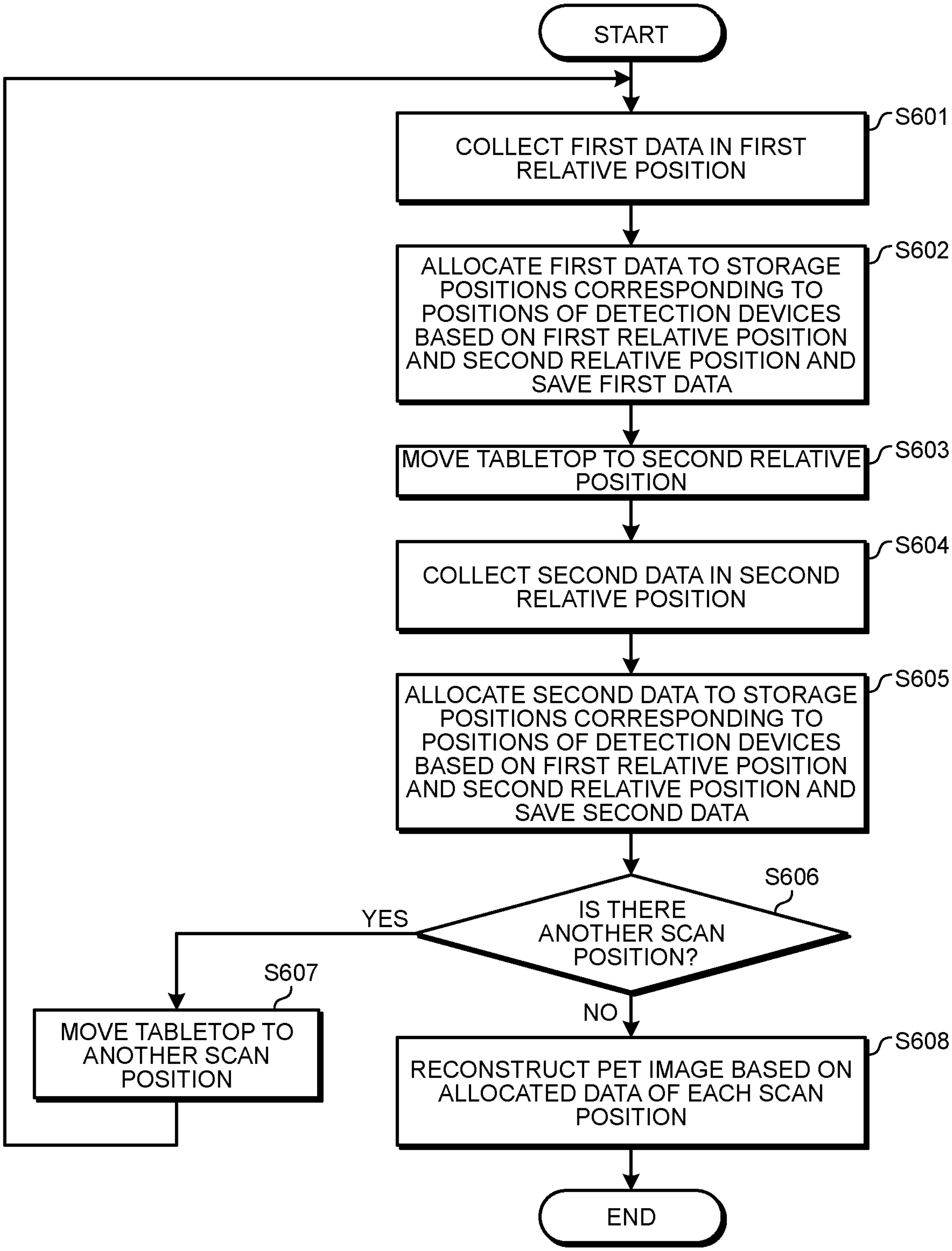
FIG. 6 is a flowchart illustrating an example of a procedure of a high-definition image generation process according to the embodiment.

FIG. 6 is a flowchart illustrating an example of a procedure of the high-definition image generation process. For specific description of the high-definition image generation process, the S&S collecting method is supposed to be executed on the subject P. Prior to execution of the high-definition image generation process, selecting of the S&S collecting method, an area of collecting by intermittent move scans, a first relative position and a second relative position (or a distance between a first relative position and a second relative position), times of collecting in the first relative position and the second relative position, a direction of move from the first relative position to the second relative position, etc., are set according to instructions of the user via the input interface 76. A subject to be moved in the high-definition image generation process is the tabletop 53. In addition to this, the direction of move is supposed to be the Z-direction for simple description.

Note that, when the user desires a high-definition PET image on a slice plane, the direction of move is set in two directions of the X-direction and the Y-direction or in diagonal directions on an X-Y plane. When the PET image is volume data and the user desires a high-definition image over the volume data, the direction of move is set in three directions of the X-direction, the Y-direction, and the Z-direction or in diagonal directions in an X-Y-Z space.

High-Definition Image Generation Process

Step S601

Using the imaging controlling function 731 or the relative position controlling function 733, the processing circuitry 73 moves the tabletop 53 to the first relative position. The data collecting function 735 (or the imaging controlling function 731) collects first data by PET scan in the first relative position. For example, when the data is collected in a time of collecting of two minutes per shoot (per bed), the data collecting function 735 (or the imaging controlling function 731) executes PET scans as usual in the first relative position as illustrated in FIG. 2 in the first one minute, thereby collecting the first data.

Step S602

Using the data collecting function 735, the processing circuitry 73 allocates the collected first data to storage positions corresponding to positions of the detection devices based on the first relative position and the second relative position (or the distance along the direction of move) and the IDs of the detection devices (scintillators Sc) and is saved in the memory 75. The process of the step may be executed after step S605 or at step S605.

Step S603

Using the relative position controlling function 733, the processing circuitry 73 controls the table drive apparatus 54 to move the position of the tabletop 53 from the first relative position RP1 to the second relative position RP2. Accordingly, as illustrated in FIG. 2, the tabletop 53 moves from the first relative position RP1 to the second relative position RP2. For example, when the width (thickness) of the scintillator Sc is 4 mm, the tabletop 53 is moved by 2 mm along the Z-direction that is the set direction of move at this step.

Step S604

Using the data collecting function 735 (or the imaging controlling function 731), the processing circuitry 73 collects second data by executing PET scan in the second relative position. For example, when the second data is collected for two minutes per shoot (per bed), the data collecting function 735 (or the imaging controlling function 731) executes PET scans as usual in the second relative position as illustrated in FIG. 2 in the last one minute, thereby collecting the second data. Note that the time of collecting at step S601 and step S504 is described as half the time of collecting per shoot (per bed); however, the time of collecting is not limited to this and, for example, any time of collecting can be set according to the trade-off between a S/N ratio in a PET image that is reconstructed and a time of PET examination on the subject P.

Step S605

Using the data collecting function 735, the processing circuitry 73 allocates the collected second data to storage positions corresponding to positions of the detection devices based on the first relative position and the second relative position (or the distance along the direction of move) and the IDs of the detection devices (scintillators Sc) and is saved in the memory 75. The process of the step may be executed after step S606.

Step S606

In intermittent move scans (the S&S method), when there is another scan position (another shoot position) (YES at step S606), the process of step S607 is executed. In intermittent move scans (the S&S method), when there is no other scan position (no another shoot position) (NO at step S606), the process of step S608 is executed.

Step S607

Using the imaging controlling function 731 or the relative position controlling function 733, the processing circuitry 73 moves the tabletop 53 to another scan position.

Another scan position corresponds to the first relative position in the next shoot. Then, the process of steps S601 to S606 is repeated.

Step S608

Using the reconstruction process function 737, the processing circuitry 73 reconstructs a PET image based on the allocated data (upsampling data) of each scan position. Specifically, the reconstruction process function 737 executes a reconstruction process using the upsampling data corresponding to each of the scan positions and generates PET images. The generated PET images are stored in the memory 75. The image processing function 739 executes image processing on the generated PET images and generates a plurality of PET slice images corresponding to a plurality of slice planes, respectively. The image processing function 739 may generate the PET slice images such that the PET slice images have a standardized uptake value (SUV) as pixel values. The display controlling function 741 displays the PET slice images on the display 74.

The nuclear medicine diagnostic apparatus 1 according to the embodiment described above controls a change from the first relative position RP1 of the nuclear medicine detector 17 including the detection devices Sc that detect gamma rays and the subject P to the second relative position RP2 that is separate from the first relative position RP1 by a distance smaller than the device size of the detection device Sc, collects the first data in the first relative position RP1, collects the second data in the second relative position RP2, and reconstructs a nuclear medicine image based on the first data and the second data. For example, the nuclear medicine diagnostic apparatus 1 according to the embodiment controls move of at least one of the nuclear medicine detector 17 and the tabletop 53 on which the subject P is laid in the change from the first relative position RP1 to the second relative position RP2.

Specifically, the nuclear medicine diagnostic apparatus 1 according to the embodiment controls move of at least one of the nuclear medicine detector 17 and the tabletop 53 along the direction containing at least one of the vertical direction, the longitudinal direction of the tabletop 53, and the transverse direction of the tabletop 53. The nuclear medicine diagnostic apparatus 1 according to the embodiment generates upsampling data with a density higher than those of the first data and the second data based on the first relative position RP1, the second relative position RP2, the first data, and the second data and reconstructs a nuclear medicine image using the upsampling data based on the first data and the second data. Using FIG. 7, an effect of the embodiment will be described below.

Figure 7:
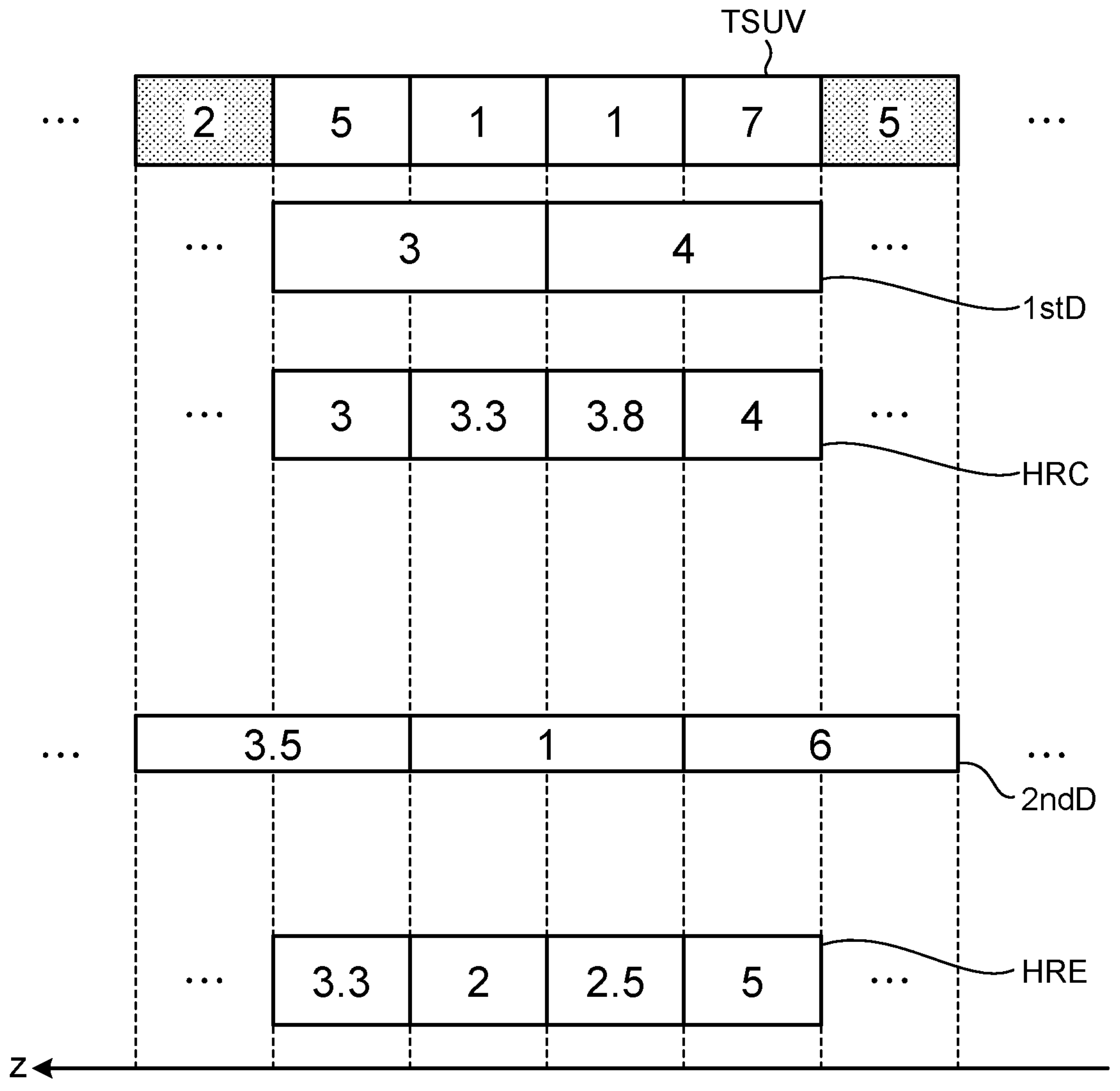
FIG. 7 is a diagram illustrating an example of an effect of the embodiment.

FIG. 7 is a diagram illustrating an example of the effect in the embodiment. FIG. 7 illustrates a one-dimensional pixel row along the Z-direction for convenience of description. The top-grade pixel row TSUV in FIG. 7, for example, presents a plurality of pixel values corresponding to a true SUV. A second-grade pixel row 1stD in FIG. 7 presents a plurality of pixel values corresponding to a SUV that is generated by reconstruction based on the first data. A third-grade pixel array HRC in FIG. 7 presents a pixel row serving as a comparative example that is generated by centroid computation with respect to the second-grade pixel row 1stD in FIG. 7.

A fourth-grade pixel array 2ndD in FIG. 7 presents a plurality of pixel values corresponding to a SUV that is generated by reconstruction based on the second data. A fifth-grade pixel row HRE in FIG. 7 presents a pixel row of a SUV in the embodiment that is generated by centroid computation on the second-grade pixel row 1stD in FIG. 7 and the fourth-grade pixel row 2ndD in FIG. 7. The fifth-grade pixel row HRE in FIG. 7 corresponds to the pixel row of the SUV in a nuclear medicine image that is generated by the high-definition image generation process.

When the top-grade pixel array TSUV in FIG. 7 is correct data, the fifth-grade pixel array HRE that is generated by the embodiment is much closer to the pixel array TSUV of the correct data than to the third-grade pixel array HRC serving as a comparative example. For this reason, according to the embodiment, using scintillators Sc for data in upsampling without segmenting the scintillators Sc makes it possible to increase accuracy of upsampling.

Thus, according to the nuclear medicine diagnostic apparatus 1 according to the embodiment, it is possible to perform accurate upsampling easily and at low cost and it is possible to provide an image with an accurately-reduced pixel size (high-definition image). For this reason, according to the nuclear medicine diagnostic apparatus 1, it is possible to increase a throughput of an examination on the subject P.

When a technical idea in the embodiment is realized using a nuclear medicine imaging method, the nuclear medicine imaging method controls a change from the first relative position RP1 of the nuclear medicine detector 17 including the detection devices Sc that detect gamma rays and the subject P to the second relative position RP2 that is separate from the first relative position RP1 by a distance smaller than the device size of the detection device Sc, collects the first data in the first relative position RP1, collects the second data in the second relative position RP2, and reconstructs a nuclear medicine image based on the first data and the second data. A procedure and effects of the nuclear medicine imaging method are similar to those of the embodiment and thus description thereof will be omitted.

When the technical idea in the present embodiment is realized using a nuclear medicine imaging program, the nuclear medicine imaging program causes a computer to realize controlling a change from the first relative position RP1 of the nuclear medicine detector 17 including the detection devices Sc that detect gamma rays and the subject P to the second relative position RP2 that is separate from the first relative position RP1 by a distance smaller than the device size of the detection device Sc, collecting the first data in the first relative position RP1, collecting the second data in the second relative position RP2, and reconstructing a nuclear medicine image based on the first data and the second data. The program that makes it possible to cause the computer to execute the method cab be stored in a storage medium, such as a magnetic disk (hard disk), an optical disk (a CD-ROM or a DVD), or a semiconductor memory, and can be distributed. The procedure and the effect of the nuclear medicine imaging program are similar to those of the embodiment and thus description thereof will be omitted.

According to at least one of the embodiments described above, or the like, it is possible to generate an accurate nuclear medicine image having a pixel size that is simply and accurately reduced without segmenting a detection device.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnostic apparatus, comprising:

a nuclear medicine detector including a plurality of detection devices that detect gamma rays; and processing circuitry configured to control a change of a position of the nuclear medicine detector relative to a subject from a first relative position to a second relative position, the second relative position being separated by a distance from the first relative position in a direction along a surface of the nuclear medicine detector that receives the gamma rays, the distance being smaller than a device size of one of the detection devices in the direction, collect first data in the first relative position, collect second data in the second relative position, and reconstruct a nuclear medicine image based on the first data and the second data.

2. The nuclear medicine diagnostic apparatus according to claim 1, wherein the processing circuitry is further configured to control movement of at least one of the nuclear medicine detector and a tabletop on which the subject is laid, in controlling the change from the first relative position to the second relative position.

3. The nuclear medicine diagnostic apparatus according to claim 2, wherein the processing circuitry is further configured to control movement of at least one of the nuclear medicine detector and the tabletop along the direction, which is a longitudinal direction of the tabletop or a transverse direction of the tabletop.

4. The nuclear medicine diagnostic apparatus according to claim 1, wherein the processing circuitry is further configured to:

generate upsampling data whose data density is higher than those of the first data and the second data based on the first relative position, the second relative position, the first data, and the second data, store the upsampling data in a memory, and reconstruct the nuclear medicine image using the upsampling data based on the first data and the second data.

5. A nuclear medicine imaging method, comprising:

controlling a change of a position of a nuclear medicine detector relative to a subject from a first relative position to a second relative position, the second relative position being separated by a distance from the first relative position in a direction along a surface of the nuclear medicine detector that receives gamma rays, the distance being smaller than a device size of one of a plurality of detection devices in the direction;

collecting first data in the first relative position and collecting second data in the second relative position; and reconstructing a nuclear medicine image based on the first data and the second data.

6. A non-transitory computer-readable storage medium that stores a nuclear medicine imaging program that causes a computer to perform a method comprising:

controlling a change of a position of a nuclear medicine detector relative to a subject from a first relative position to a second relative position, the second relative position being separated by a distance from the first relative position in a direction along a surface of the nuclear medicine detector that receives gamma rays, the distance being smaller than a device size of one of a plurality of detection devices in the direction, collecting first data in the first relative position and collecting second data in the second relative position, and reconstructing a nuclear medicine image based on the first data and the second data.

* * * * *